(12) United States Patent
Marion et al.

(10) Patent No.: US 8,765,101 B2
(45) Date of Patent: Jul. 1, 2014

(54) PHOTOPROTECTIVE COMPOSITION BASED ON A 2-ALKOXY-4-ALKYL KETONE PHENOL COMPOUND; USE OF SAID COMPOUND FOR INCREASING THE SUN PROTECTION FACTOR

(75) Inventors: Catherine Marion, Antony (FR); Geraldine Lerebour, Les Loges en Josas (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/500,755

(22) PCT Filed: Sep. 30, 2010

(86) PCT No.: PCT/EP2010/064596
§ 371 (c)(1),
(2), (4) Date: Jun. 27, 2012

(87) PCT Pub. No.: WO2011/042358
PCT Pub. Date: Apr. 14, 2011

(65) Prior Publication Data
US 2012/0263768 A1      Oct. 18, 2012

Related U.S. Application Data

(60) Provisional application No. 61/272,646, filed on Oct. 15, 2009.

(30) Foreign Application Priority Data

Oct. 8, 2009   (FR) ..................................... 09 57016

(51) Int. Cl.
*A61Q 17/04*        (2006.01)

(52) U.S. Cl.
CPC ..................................... *A61Q 17/04* (2013.01)
USPC .......................................................... 424/59

(58) Field of Classification Search
CPC ..................................................... A61Q 17/04
See application file for complete search history.

(56) References Cited

U.S. PATENT DOCUMENTS

| | | | |
|---|---|---|---|
| 7,431,917 B2 * | 10/2008 | Candau | 424/59 |
| 2003/0017997 A1 * | 1/2003 | Yokota et al. | 514/25 |
| 2009/0149550 A1 * | 6/2009 | Sugita et al. | 514/678 |
| 2012/0269739 A1 * | 10/2012 | Dalko et al. | 424/43 |

* cited by examiner

*Primary Examiner* — Susan Tran
(74) *Attorney, Agent, or Firm* — Novak Druce Connolly Bove + Quigg LLP

(57) ABSTRACT

The present invention relates to a fluid composition intended for protecting the skin and/or hair against ultraviolet radiation, characterized by the fact that it comprises, in a cosmetically acceptable aqueous support, at least: (a) one photoprotective system capable of screening out UV radiation; and (b) one 2-alkoxy-4-alkyl ketone phenol compound. The present invention also relates to the use of a 2-alkoxy-4-alkyl ketone phenol compound in a composition comprising, in a cosmetically acceptable medium, at least one photoprotective system capable of screening out UV radiation.

21 Claims, No Drawings

PHOTOPROTECTIVE COMPOSITION BASED ON A 2-ALKOXY-4-ALKYL KETONE PHENOL COMPOUND; USE OF SAID COMPOUND FOR INCREASING THE SUN PROTECTION FACTOR

CROSS REFERENCE TO RELATED APPLICATIONS

This application is a National Phase filing under 35 U.S.C. §371 of PCT/FR2010/064506 filed on Sep. 30, 2010; and this application claims priority to application No. 0957016 filed in France on Oct. 8, 2009 under 35 U.S.C. §119, and claims the benefit of U.S. Provisional Application No. 61/272,646 filed on Oct. 15, 2009; the entire contents of all are hereby incorporated by reference.

The present invention relates to a fluid composition intended for protecting the skin and/or hair against ultraviolet radiation, characterized by the fact that it comprises, in a cosmetically acceptable aqueous support, at least:

(a) one photoprotective system capable of screening out UV radiation; and (b) one 2-alkoxy-4-alkyl ketone phenol compound.

The present invention also relates to the use of a 2-alkoxy-4-alkyl ketone phenol compound in a composition comprising, in a cosmetically acceptable medium, at least one photoprotective system capable of screening out UV radiation.

It is known that light radiation with wavelengths of between 280 nm and 400 nm permits tanning of the human epidermis and that rays with wavelengths of between 280 and 320 nm, which are known as UV-B rays, cause skin burns and erythema that can harm the development of a natural tan; this UV-B radiation should thus be screened out.

It is also known that UV-A rays, with wavelengths of between 320 and 400 nm, which cause tanning of the skin, are liable to induce impairment thereof, especially in the case of sensitive skin or of skin that is continually exposed to solar radiation. UV-A rays in particular cause a loss of skin elasticity and the appearance of wrinkles, leading to premature ageing. They promote the onset of the erythematous reaction or amplify this reaction in the case of certain individuals, and may even be the cause of phototoxic or photoallergic reactions. It is thus desirable also to screen out UV-A radiation.

Many photoprotective (UV-A and/or UV-B) cosmetic compositions for the skin have been proposed to date. Fluid formulations that afford for the users easy application to skin are most particularly sought.

These antisun fluid compositions are quite often in the form of an emulsion of oil-in-water type (i.e. a cosmetically acceptable support constituted of an aqueous dispersing continuous phase and of an oily dispersed discontinuous phase) that contains, in varying concentrations, one or more standard lipophilic and/or hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent, to the dose of UV radiation required to reach the erythema-forming threshold without UV-screening agent.

Thus, there is still a significant need to find antisun products that have a sufficiently high protection factor. High protection factors may be reached by incorporating more screening agents in high concentrations. This is not always achievable, despite the addition of large amounts of screening agents. Furthermore, such amounts may result in impairment of the comfort (tacky, coarse effect and/or greasy effect).

After considerable research conducted in the field of photoprotection mentioned above, the Applicant has now discovered, surprisingly, that the addition of a 2-alkoxy-4-alkyl ketone phenol compound, in a composition containing at least one system for screening out UV radiation, made it possible to increase its photoprotection efficacy and in particular its sun protection factor.

This discovery forms the basis of the present invention.

Thus, in accordance with a first subject of the present invention, novel fluid compositions for protecting the skin and/or hair against ultraviolet radiation are proposed, characterized by the fact that they comprise, in a cosmetically acceptable aqueous support, at least:

(a) one photoprotective system capable of screening out UV radiation constituted by one or more hydrophilic, lipophilic or insoluble organic screening agents and/or one or more metal oxide pigments which may or may not be coated;

(b) at least one 2-alkoxy-4-alkyl ketone phenol compound.

According to the invention, the term "photoprotective system capable of screening out UV radiation" is generally intended to denote any compound or any combination of compounds which, via mechanisms known per se of absorption and/or reflection and/or scattering of UV-A and/or UV-B radiation, makes it possible to prevent, or at least to limit, the contact of said radiation with a surface (skin or hair) onto which this or these compound(s) have been applied. In other words, these compounds may be UV-absorbing photoprotective organic screening agents or UV-scattering and/or UV-reflecting mineral pigments, and also mixtures thereof.

The term "cosmetically acceptable" means compatible with the skin and/or its integuments, which has a pleasant colour, odour and feel and which does not cause any unacceptable discomfort (stinging, tautness or redness) liable to put the consumer off using this composition.

Yet another subject of the present invention lies in the use of at least one 2-alkoxy-4-alkyl ketone phenol compound in a fluid composition comprising, in a cosmetically acceptable support, at least one photoprotective system capable of screening out UV radiation constituted by one or more hydrophilic, lipophilic or insoluble organic screening agents and/or one or more metal oxide pigments which may or may not be coated, for the purpose of increasing the sun protection factor (SPF).

Other features, aspects and advantages of the present invention will emerge on reading the detailed description that follows.

Preferably, the 2-alkoxy-4-alkyl ketone phenol compounds in accordance with the invention are chosen from those corresponding to the formula (I) below:

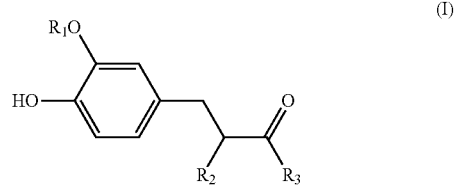

in which $R_1$ represents a (saturated) linear $C_1$-$C_4$ alkyl radical, and preferably methyl or ethyl;

$R_2$ represents a hydrogen atom or a (saturated) linear $C_1$-$C_4$ alkyl radical, and preferably methyl or ethyl;

R₃ represents a (saturated) linear $C_1$-$C_{12}$ alkyl radical, optionally substituted by a hydroxyl group; or else an (unsaturated C=C) linear $C_2$-$C_{12}$ alkenyl radical, optionally substituted by a hydroxyl group.

Preferably, the compounds correspond to the formula (I) in which:

$R_2$ is chosen from H and $CH_3$; better still $R_2$ denotes hydrogen; and/or $R_3$ represents (i) a $C_1$-$C_{10}$ alkyl radical; (ii) a $C_2$-$C_{10}$ alkenyl radical, in particular a —CH=CH—$R_4$ radical with $R_4$ representing a linear $C_1$-C alkyl radical; or else (iii) a hydroxyalkyl radical of structure —$CH_2$—CH(OH)—$R_5$ with $R_5$ representing a linear $C_1$-$C_{10}$, preferably $C_4$-$C_{10}$, alkyl radical.

The compounds of formula (I) that are particularly preferred are the following:

(a)
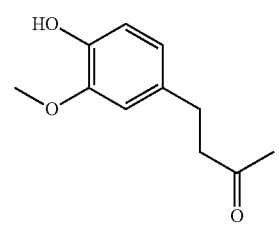

(b)
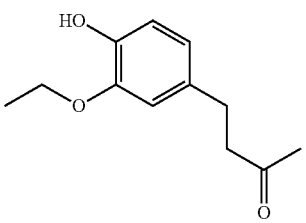

(c)
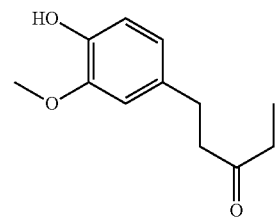

(d)
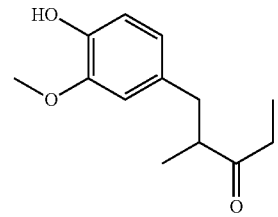

(e)
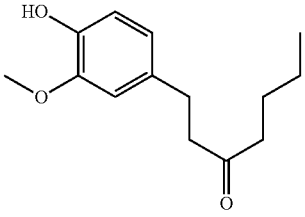

-continued (f)
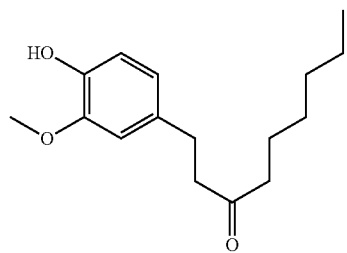

(g)
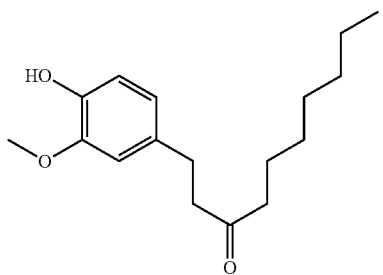

(h)
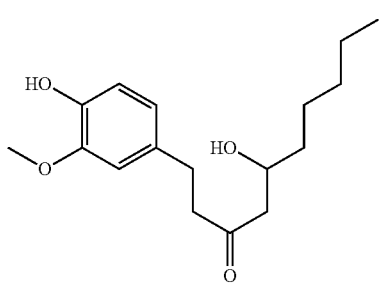

(i)
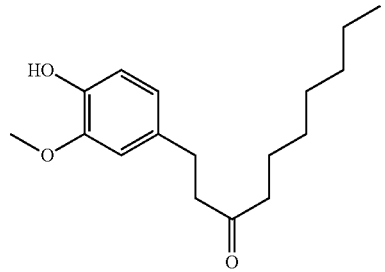

(j)
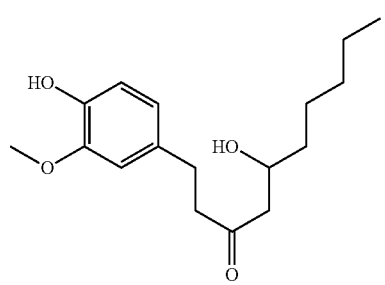

(k)
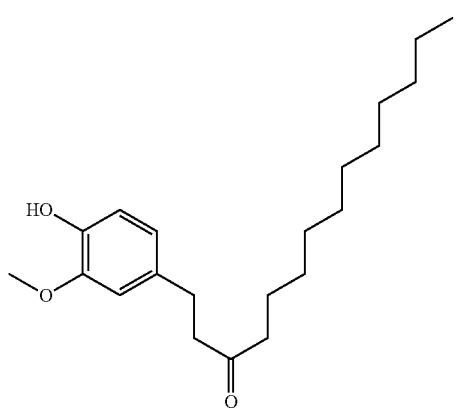

(l)
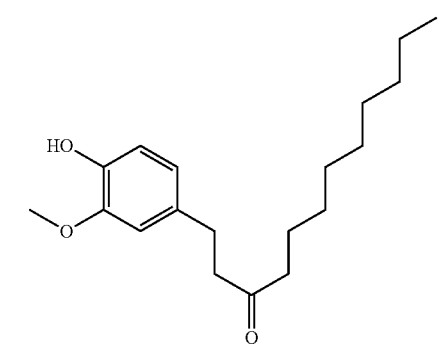

(m)
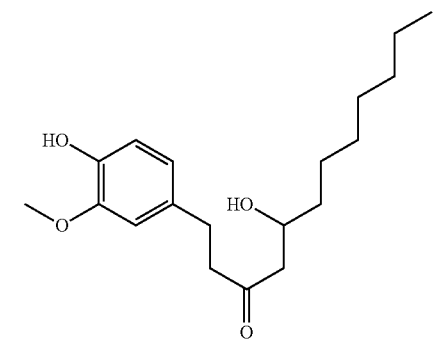

(n)
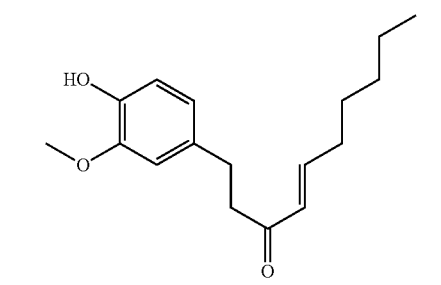

(o)
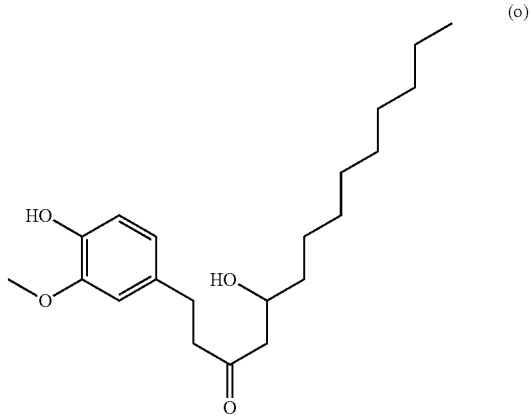

(p)
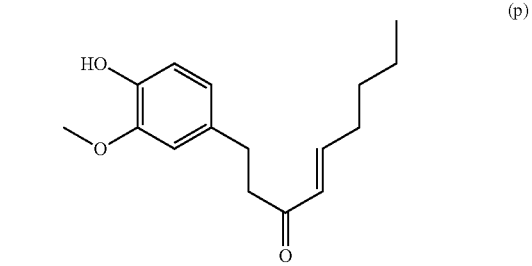

(q)
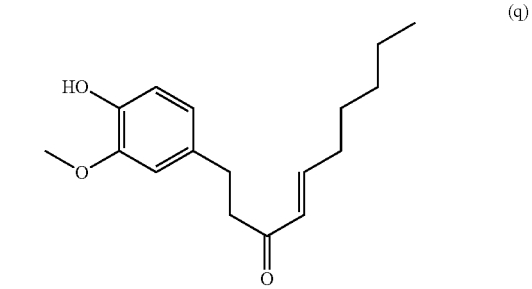

According to one particularly preferred form of the invention, use will be made of the compound 4-(3-methoxy-4-hydroxyphenyl)butane-2-one also known as gingerone (INCI name: ZINGERONE) or vanillylacetone.

The compounds of formula (I) can be easily prepared by a person skilled in the art on the basis of his general knowledge. Mention may especially be made of the following bibliographic references: J. Asian Natural Products Research, 2006, 8(8), 683-688; Helv. Chimica Acta, 2006, 89(3), 483-495; Chem. Pharm. Bull., 2006, 54(3), 377-379; and Bioorg. Med. Chem. Lett., 2004, 14(5), 1287-1289.

The compounds may thus be prepared from vanillin or ethylvanillin (commercial products) in the following manner:

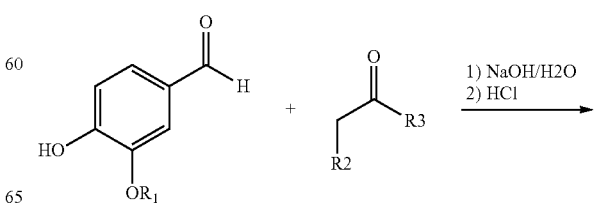

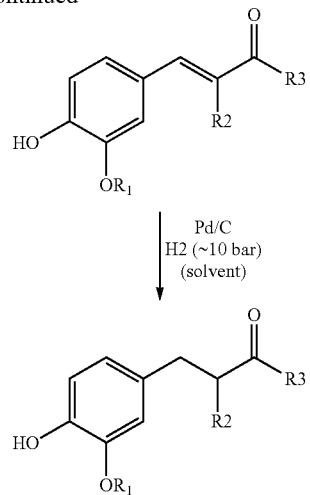

R1 = methyl, CAS: 121-33-5
   ethyl, CAS: 121-32-4

The 2-alkoxy-4-alkyl ketone phenol compound(s) in accordance with the invention is (are) present in the composition preferably from 0.01 to 10% by weight and more preferably still from 0.5 to 5% and more particularly still from 1 to 3% relative to the total weight of the composition.

According to the invention, the photoprotective system may be constituted of one or more hydrophilic, lipophilic or insoluble organic screening agents and/or one or more mineral pigments. Preferentially, it will be constituted of at least one hydrophilic, lipophilic or insoluble organic UV-screening agent.

The organic screening agents are chosen especially from dibenzoylmethane derivatives; anthranilates; cinnamic derivatives; salicylic derivatives; camphor derivatives; benzophenone derivatives; β,β-diphenyl-acrylate derivatives; triazine derivatives other than those of formula (I); benzmalonate derivatives, especially those cited in U.S. Pat. No. 5,624,663; benzimidazole derivatives; imidazolines; p-aminobenzoic acid (PABA) derivatives; benzotriazole derivatives; methylene bis(hydroxyphenylbenzotriazole) derivatives as described in applications U.S. Pat. Nos. 5,237,071, 166,355, GB 2 303 549, DE 19726184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; dimers derived from α-alkyl-styrene such as those described in patent application DE 19855649; 4,4-diarylbutadienes such as those described in patent applications EP 0 967 200, DE 19746654, DE 19755649, EP-A-1 008 586, EP 1 133 980 and EP 133 981, merocyanine derivatives such as those described in patent applications WO 04/006878, WO 05/058269 and WO 06/032741; indanylidene screening agents from patents EP-A-0 823 418 and EP-A-1 341 752.

As examples of organic UV-screening agents, mention may be made of those denoted hereinbelow under their INCI name:

Dibenzoylmethane Derivatives:
  Butyl Methoxydibenzoylmethane offered for sale under the trade name "Parsol 1789" by the company DSM Nitritional Products.
para-Aminobenzoic Acid Derivatives:
  PABA,
  Ethyl PABA,
  Ethyl Dihydroxypropyl PABA,
  Ethylhexyl dimethyl PABA sold in particular under the name "Escalol 507" by ISP,
  Glyceryl PABA,
  PEG-25 PABA sold under the name "Uvinul P25" by BASF.
Salicylic Derivatives:
  Homosalate sold under the name "Eusolex HMS" by Rona/EM Industries,
  Ethylhexyl Salicylate sold under the name "Neo Heliopan OS" by Symrise,
  Dipropylene Glycol Salicylate sold under the name "Dipsal" by Scher,
  TEA Salicylate sold under the name "Neo Heliopan TS" by Symrise.
Cinnamic Derivatives:
  Ethylhexyl Methoxycinnamate sold in particular under the trade name "Parsol MCX" by DSM Nutritional Products,
  Isopropyl Methoxycinnamate,
  Isoamyl Methoxycinnamate sold under the trade name "Neo Heliopan E 1000" by Symrise,
  Cinoxate,
  DEA Methoxycinnamate,
  Diisopropyl Methylcinnamate,
  Glyceryl Ethylhexanoate Dimethoxycinnamate.
β,β-Diphenylacrylate Derivatives:
  Octocrylene sold in particular under the trade name "Uvinul N539" by BASF,
  Etocrylene sold in particular under the trade name "Uvinul N35" by BASF.
Benzophenone Derivatives:
  Benzophenone-1 sold under the trade name "Uvinul 400" by BASF,
  Benzophenone-2 sold under the trade name "Uvinul D50" by BASF,
  Benzophenone-3 or Oxybenzone sold under the trade name "Uvinul M40" by BASF,
  Benzophenone-4 sold under the trade name "Uvinul MS40" by BASF,
  Benzophenone-5,
  Benzophenone-6 sold under the trade name "Helisorb 11" by Norquay,
  Benzophenone-8 sold under the trade name "Spectra-Sorb UV-24" by American Cyanamid,
  Benzophenone-9 sold under the trade name "Uvinul DS-49" by BASF,
  Benzophenone-12,
  n-Hexyl 2-(4-diethylamino-2-hydroxybenzoyl)-benzoate sold under the trade name "Uvinul A+" or in the form of a mixture with octyl methoxycinnamate under the trade name "Uvinul A+B" by BASF.
Benzylidenecamphor Derivatives:
  3-Benzylidene Camphor manufactured under the name "Mexoryl SD" by Chimex,
  4-Methylbenzylidene Camphor sold under the name "Eusolex 6300" by Merck,
  Benzylidene Camphor Sulfonic Acid manufactured under the name "Mexoryl SL" by Chimex,
  Camphor Benzalkonium Methosulfate manufactured under the name "Mexoryl SO" by Chimex, Terephthalylidene Dicamphor Sulfonic Acid manufactured under the name "Mexoryl SX" by Chimex, Polyacrylamidomethyl Benzylidene Camphor manufactured under the name "Mexoryl SW" by Chimex.

Phenylbenzimidazole Derivatives:

Phenylbenzimidazole Sulfonic Acid sold in particular under the trade name "Eusolex 232" by Merck, Disodium Phenyl Dibenzimidazole Tetrasulfonate sold under the trade name "Neo Heliopan AP" by Symrise.

Benzotriazole Derivatives:

Drometrizole Trisiloxane sold under the name "Silatrizole" by Rhodia Chimie,

Methylene bis-Benzotriazolyl Tetramethylbutyl-phenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:

bis-Ethylhexyloxyphenol Methoxyphenyl Triazine sold under the trade name "Tinosorb S" by Ciba Geigy, Ethylhexyl Triazone sold in particular under the trade name "Uvinul T150" by BASF, Diethylhexyl Butamido Triazone sold under the trade name "Uvasorb HEB" by Sigma 3V, 2,4-bis(n-butyl 4'-benzalmalonate)-6-[(3-{1,3,3,3-tetramethyl-1-[(trimethylsilyl)oxy]disiloxanyl}propyl)amino]-s-triazine, 2,4,6-tris(diisobutyl 4'-aminobenzalmalonate)-s-triazine, 2,4,6-tris(dineopentyl 4'-aminobenzalmalonate)-s-triazine, 2,4-bis(dineopentyl 4'-aminobenzalmalonate)-6-(n-butyl 4'-aminobenzoate)-s-triazine, symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc., West Henrietta, N.Y., US (20 Sep. 2004), especially 2,4,6-tris(biphenyl)-1,3,5-triazines (in particular 2,4,6-tris(biphenyl-4-yl)-1,3,5-triazine and 2,4,6-tris(terphenyl)-1,3,5-triazine, which is included in Beiersdorf applications WO 06/035000, WO 06/034982, WO 06/034991, WO 06/035007, WO 2006/034992 and WO 2006/034985).

Anthranilic Derivatives:

Menthyl Anthranilate sold under the trade name "Neo Heliopan MA" by Symrise.

Imidazoline Derivatives:

Ethylhexyl Dimethoxybenzylidene Dioxoimidazoline Propionate.

Benzalmalonate Derivatives:

Di-neopentyl 4'-methoxybenzalmalonate

Polyorganosiloxane containing benzalmalonate functions, for instance Polysilicone-15, sold under the trade name "Parsol SLX" by DSM Nutritional Products.

4,4-Diarylbutadiene Derivatives:

1,1-dicarboxy(2,2'-dimethylpropyl)-4,4-diphenyl-butadiene.

Benzoxazole Derivatives:

2,4-bis[5-(1-dimethylpropyl)benzoxazol-2-yl-(4-phenyl)imino]-6-(2-ethylhexyl)imino-1,3,5-triazine sold under the name Uvasorb K2A by Sigma 3V, and mixtures thereof.

The preferential organic screening agents are chosen from:

Ethylhexyl Methoxycinnamate,
Homosalate,
Ethylhexyl Salicylate,
Octocrylene,
Butyl Methoxydibenzoylmethane,
Terephthalylidene Dicamphor Sulfonic Acid,
Disodium Phenyl Dibenzimidazole Tetrasulfonate,
Phenylbenzimidazole Sulfonic Acid,
Benzophenone-3,
n-Hexyl 2-(4-diethylamino-2-hydroxybenzoyl)-benzoate,
4-Methylbenzylidene Camphor,
Ethylhexyl triazone,
Bis-Ethylhexyloxyphenol Methoxyphenyl Triazine,
Diethylhexyl Butamido Triazone,
2,4-bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(biphenyl-4-yl)-1,3,5-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
Methylene Bis-Benzotriazolyl Tetramethylbutyl-phenol,
Drometrizole Trisiloxane,
Polysilicone-15,
Di-neopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl)imino]-6-(2-ethylhexyl)imino-1,3,5-triazine, and mixtures thereof.

The complementary inorganic screening agents are chosen from coated or uncoated metal oxide pigments for which the mean size of the primary particles is preferentially between 5 nm and 100 nm (preferably between 10 nm and 50 nm) such as, for example, pigments formed of titanium oxide (amorphous or crystalline in the rutile and/or anatase form), of iron oxide, of zinc oxide, of zirconium oxide or of cerium oxide, which are all UV photoprotective agents well known per se.

The pigments may be coated or uncoated.

The coated pigments are pigments that have undergone one or more surface treatments of chemical, electronic, mechanochemical and/or mechanical nature with compounds as described for example in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (of titanium or of aluminium), polyethylene, silicones, proteins (collagen, elastin), alkanolamines, silicon oxides, metal oxides or sodium hexametaphosphate.

In a known way, the silicones are organosilicon polymers or oligomers having a linear or cyclic and branched or crosslinked structure, of variable molecular weight, obtained by polymerization and/or polycondensation of suitably functionalized silanes and essentially constituted of a repetition of main units in which the silicon atoms are connected to one another via oxygen atoms (siloxane bond), optionally substituted hydrocarbon radicals being connected directly to said silicon atoms via a carbon atom.

The term "silicones" also encompasses the silanes necessary for their preparation, in particular alkylsilanes.

The silicones used for the coating of the pigments suitable for the present invention are preferably chosen from the group containing alkylsilanes, polydialkylsiloxanes and polyalkylhydrosiloxanes. More preferably still, the silicones are chosen from the group containing octyltrimethylsilane, polydimethylsiloxanes and polymethylhydrosiloxanes.

Of course, the metal oxide pigments formed may, before their treatment with silicones, have been treated with other surface agents, in particular with cerium oxide, alumina, silica, aluminium compounds, silicon compounds or mixtures thereof.

The coated pigments are more particularly titanium oxides that have been coated:
- with silica, such as the product "Sunveil" from the company Ikeda and the product "Eusolex T-AVO" from the company Merck,
- with silica and iron oxide, such as the product "Sunveil F" from the company Ikeda,
- with silica and alumina, such as the products "Microtitanium Dioxide MT 500 SA" and "Microtitanium Dioxide MT 100 SA" from the company Tayca and "Tioveil" from the company Tioxide, and "Mirasun TiW 60 from the company Rhodia,
- with alumina, such as the products "Tipaque TTO-(B)" and "Tipaque TTO-55 (A)" from the company Ishihara and "UVT 14/4" from the company Kemira,
- with alumina and aluminium stearate, such as the products "Microtitanium Dioxide MT 100 T, MT 100 TX, MT 100 Z and MT-01" from the company Tayca, the products "Solaveil CT-10 W", "Solaveil CT 100" and "Solaveil CT 200" from the company Uniqema,
- with silica, alumina and alginic acid, such as the product "MT-100 AQ" from the company Tayca,
- with alumina and aluminium laurate, such as the product "Microtitanium Dioxide MT 100 S" from the company Tayca,
- with iron oxide and iron stearate, such as the product "Microtitanium Dioxide MT 100 F" from the company Tayca,
- with zinc oxide and zinc stearate, such as the product "BR351" from the company Tayca,
- with silica and alumina and treated with a silicone, such as the products "Microtitanium Dioxide MT 600 SAS", "Microtitanium Dioxide MT 500 SAS" or "Microtitanium Dioxide MT 100 SAS" from the company Tayca,
- with silica, alumina and aluminium stearate and treated with a silicone, such as the product "STT-30-DS" from the company Titan Kogyo,
- with silica and treated with a silicone, such as the product "UV-Titan X 195" from the company Kemira, or the product "SMT-100 WRS" from the company Tayca,
- with alumina and treated with a silicone, such as the products "Tipaque TTO-55 (S)" from the company Ishihara or "UV Titan M 262" from the company Kemira,
- with triethanolamine, such as the product "STT-65-S" from the company Titan Kogyo,
- with stearic acid, such as the product "Tipaque TTO-55 (C)" from the company Ishihara,
- with sodium hexametaphosphate, such as the product "Microtitanium Dioxide MT 150 W" from the company Tayca.

Other titanium oxide pigments treated with a silicone are preferably $TiO_2$ treated with octyltrimethylsilane and for which the mean size of the elementary particles is between 25 and 40 nm, such as that sold under the trade name "T 805" by the company Degussa Silices, $TiO_2$ treated with a polydimethylsiloxane and for which the mean size of the elementary particles is 21 nm, such as that sold under the trade name "70250 Cardre UF $TiO_2Si_3$" by the company Cardre, anatase/rutile $TiO_2$ treated with a polydimethylhydrosiloxane and for which the mean size of the elementary particles is 25 nm, such as that sold under the trade name "Microtitanium Dioxide USP Grade Hydrophobic" by the company Color Techniques.

The uncoated titanium oxide pigments are sold, for example, by the company Tayca under the trade names "Microtitanium Dioxide MT 500 B" or "Microtitanium Dioxide MT 600 B", by the company Degussa under the name "P 25", by the company Wackher under the name "Transparent titanium oxide PW", by the company Miyoshi Kasei under the name "UFTR", by the company Tomen under the name "ITS" and by the company Tioxide under the name "Tioveil AQ".

The uncoated zinc oxide pigments are, for example:
- those sold under the name "Z-Cote" by the company Sunsmart;
- those sold under the name "Nanox" by the company Elementis;
- those sold under the name "Nanogard WCD 2025" by the company Nanophase Technologies.

The coated zinc oxide pigments are, for example:
- those sold under the name "Z-Cote HP1" by the company Sunsmart (dimethicone-coated ZnO);
- those sold under the name "Zinc Oxide CS-5" by the company Toshibi (ZnO coated with polymethyl-hydrogensiloxane);
- those sold under the name "Nanogard Zinc Oxide FN" by the company Nanophase Technologies (as a 40% dispersion in Finsolv TN, $C_{12}$-$C_{15}$ alkyl benzoate);
- those sold under the name "Daitopersion Zn-30" and "Daitopersion Zn-50" by the company Daito (dispersions in cyclopolymethylsiloxane/oxyethylenated polydimethylsiloxane, containing 30% or 50% of nanozinc oxides coated with silica and polymethylhydrogensiloxane);
- those sold under the name "NFD Ultrafine ZnO" by the company Daikin (ZnO coated with perfluoroalkyl phosphate and copolymer based on perfluoroalkylethyl as a dispersion in cyclopentasiloxane);
- those sold under the name "SPD-Z1" by the company Shin-Etsu (ZnO coated with silicone-grafted acrylic polymer, dispersed in cyclodimethylsiloxane);
- those sold under the name "Escalol 2100" by the company ISP (alumina-treated ZnO dispersed in an ethylhexyl methoxycinnamate/PVP-hexadecene copolymer/methicone mixture);
- those sold under the name "Fuji ZnO-SMS-10" by the company Fuji Pigment (ZnO coated with silica and polymethylsilsesquioxane);
- those sold under the name "Nanox Gel TN" by the company Elementis (ZnO dispersed at a concentration of 55% in $C_{12}$-$C_{15}$ alkyl benzoate with hydroxystearic acid polycondensate).

The uncoated cerium oxide pigments are sold under the name "Colloidal Cerium Oxide" by the company Rhone-Poulenc.

The uncoated iron oxide pigments are sold, for example, by the company Arnaud under the names "Nanogard WCD 2002 (FE 45B)", "Nanogard Iron FE 45 BL AQ", "Nanogard FE 45R AQ" and "Nanogard WCD 2006 (FE 45R)" or by the company Mitsubishi under the name "TY-220".

The coated iron oxide pigments are sold, for example, by the company Arnaud under the names "Nanogard WCD 2008 (FE 45B FN)", "Nanogard WCD 2009 (FE 45B 556)", "Nanogard FE 45 BL 345" and "Nanogard FE 45 BL" or by the company BASF under the name "Transparent Iron Oxide".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil A", and also the alumina-, silica- and silicone-coated mixture of titanium dioxide and of zinc dioxide, such as the product "M 261" sold by the company Kemira, or the alumina-, silica- and glycerol-coated mixture of titanium dioxide and of zinc dioxide, such as the product "M 211" sold by the company Kemira.

The additional UV screening agents are generally present in the compositions according to the invention in proportions ranging from 0.01 to 20% by weight, relative to the total weight of the composition, and preferably ranging from 0.1 to 10% by weight, relative to the total weight of the composition.

The photoprotective system according to the invention is preferably present in the compositions according to the invention in a content ranging from 0.1% to 40% by weight and in particular from 5% to 25% by weight relative to the total weight of the composition.

The aqueous compositions in accordance with the present invention may also comprise standard cosmetic adjuvants chosen especially from fatty substances, organic solvents, ionic or nonionic, hydrophilic or lipophilic thickeners, demulcents, humectants, opacifiers, stabilizers, cosmetic or dermatological active agents, emollients, silicones, antifoaming agents, preservatives, anionic, cationic, nonionic, zwitterionic or amphoteric surfactants, fillers, polymers, propellants, acidifying or basifying agents or any other ingredient usually used in cosmetics and/or dermatology.

The fatty substances may be constituted of an oil or a wax other than the apolar waxes as defined above, or mixtures thereof. The term "oil" means a compound that is liquid at room temperature. The term "wax" means a compound that is solid or substantially solid at room temperature and whose melting point is generally greater than 35° C.

Oils that may be mentioned include mineral oils (paraffin); plant oils (sweet almond oil, *macadamia* oil, blackcurrant seed oil or jojoba oil); synthetic oils such as perhydrosqualene, alcohols, fatty acids or fatty esters such as the $C_{12}$-$C_{15}$ alkyl benzoate sold under the trade name "Finsolv TN" or "Witconol TN" by the company Witco, 2-ethylphenyl benzoate such as the commercial product sold under the name X-Tend 226° by the company ISP, octyl palmitate, isopropyl lanolate and triglycerides, including capric/caprylic acid triglycerides, and dicaprylyl carbonate sold under the name "Cetiol CC" by the company Cognis, oxyethylenated or oxypropylenated fatty esters and ethers; silicone oils (cyclomethicone and polydimethylsiloxanes, or PDMS) or fluoro oils, polyalkylenes and trialkyl trimellitates such as tridecyl trimellitate.

Waxy compounds that may be mentioned include carnauba wax, beeswax, hydrogenated castor oil, polyethylene waxes and polymethylene waxes, for instance the product sold under the name Cirebelle 303 by the company Sasol.

Among the organic solvents that may be mentioned are lower alcohols and polyols. The latter may be chosen from glycols and glycol ethers, for instance ethylene glycol, propylene glycol, butylene glycol, dipropylene glycol or diethylene glycol.

Hydrophilic thickeners that may be mentioned include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexa-decane/polysorbate 80) by the company SEPPIC;

2-acrylamido-2-methylpropanesulphonic acid polymers and copolymers, which are optionally crosslinked and/or neutralized, for instance the poly(2-acrylamido-2-methylpropanesulphonic acid) sold by the company Clariant under the trade name "Hostacerin AMPS" (CTFA name: ammonium polyacryloyldimethyltaurate) or Simulgel 800 sold by the company SEPPIC (CTFA name: sodium polyacryloyldimethyltaurate/polysorbate 80/sorbitan oleate); copolymers of 2-acrylamido-2-methylpropane-sulphonic acid and of hydroxyethyl acrylate, for instance Simulgel NS and Sepinov EMT 10 sold by the company SEPPIC; cellulose-based derivatives such as hydroxyethyl cellulose; polysaccharides and especially gums such as xanthan gum; water-soluble or water-dispersible silicone-based derivatives such as acrylic silicones, silicone polyethers and cationic silicones, and mixtures thereof.

Lipophilic thickeners that may be mentioned include synthetic polymers such as poly($C_{10}$-$C_{30}$ alkyl acrylates) sold under the name "Intelimer IPA 13-1" and "Intelimer IPA 13-6" by the company Landec, or modified clays such as hectorite and its derivatives, for instance the products sold under the Bentone names.

As will be appreciated, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to techniques that are well known to those skilled in the art. They may be in particular in the form of a simple or complex emulsion (O/W, W/O, O/W/O or W/O/W) such as a cream or a milk; or in the form of a lotion. They may optionally be packaged as an aerosol and may be in the form of a mousse or a spray.

The compositions according to the invention are preferably in the form of an oil-in-water or water-in-oil emulsion.

The emulsions generally contain at least one emulsifier chosen from amphoteric, anionic, cationic or nonionic emulsifiers, which are used alone or as a mixture. The emulsifiers are appropriately chosen according to the emulsion to be obtained (W/O or O/W). The emulsions may also contain stabilizers of other types, for instance fillers, gelling polymers or thickeners.

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name "DC 5225 C" by the company Dow Corning, and alkyldimethicone copolyols such as laurylmethicone copolyol sold under the name "Dow Corning 5200 Formulation Aid" by the company Dow Corning; cetyl-dimethicone copolyol, such as the product sold under the name Abil EM 90R by the company Goldschmidt, and the mixture of cetyldimethicone copolyol, of poly-glyceryl isostearate (4 mol) and of hexyl laurate, sold under the name Abil WE 09 by the company Goldschmidt. One or more co-emulsifiers may also be added thereto, which may be chosen advantageously from the group comprising polyol alkyl esters. Mention may also be made of Octyldodecanol (and) Octyldodecyl Xyloside (Fluidanov 20x), Polyglyceryl-2 Dipolyhydroxystearate (Dehymuls PGPH), Polyglyceryl-3 Ricinoleate (Akoline PGPR) and Polyglyceryl-3 Diisostearate (Lameform TG1).

Polyol alkyl esters that may especially be mentioned include polyethylene glycol esters, for instance PEG-30 Dipolyhydroxystearate, such as the product sold under the name Arlacel P135 by the company ICI.

Glycerol and/or sorbitan esters that may be mentioned include, for example, polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkyl-enated (oxyethylenated and/or oxypropylenated) fatty acid esters, for instance the mixture PEG-100 Stearate/Glyceryl Stearate sold, for example, by the company ICI under the name Arlacel 165; oxyalkylenated (oxyethylenated and/or oxypropylenated) fatty alcohol ethers; sugar esters, for instance sucrose stearate; fatty alcohol ethers of sugars, especially alkyl polyglucosides (APGs) such as decyl glucoside and lauryl glucoside sold, for example, by the company Henkel under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Goldschmidt and under the name Emulgade KE3302 by the company Henkel, and also arachidyl glucoside, for example in the form of a mixture of arachidyl alcohol, behenyl alcohol and arachidyl glucoside, sold under the name Montanov 202 by the company SEPPIC. According to one particular embodiment of the invention, the mixture of the alkyl polyglucoside as defined above with the corresponding fatty alcohol may be in the form of a self-emulsifying composition as described, for example, in document WO-A-92/06778. Mention may also be made of lecithins and derivatives (e.g. Biophilic), sugar esters and sodium stearoyl lactylate.

Among the other emulsion stabilizers, use will more particularly be made of isophthalic acid or sulphoisophthalic acid polymers, and in particular phthalate/sulphoisophthalate/glycol copolymers, for example the diethylene glycol/phthalate/isophthalate/1,4-cyclohexanedimethanol copolymer (INCI name: Polyester-5) sold under the name "Eastman AQ Polymer" (AQ35S, AQ38S, AQ55S and AQ48 Ultra) by the company Eastman Chemical.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention is constituted of the use of the compositions according to the invention as defined above for the manufacture of cosmetic products for treating the skin, the lips, the nails, the hair, the eyelashes, the eyebrows and/or the scalp, especially care products, sun protection products and makeup products.

The cosmetic compositions according to the invention may be used, for example, as makeup products.

The cosmetic compositions according to the invention may be used, for example, as a care product and/or sun protection product for the face and/or body having a liquid to semi-liquid consistency, such as milks, more or less rich creams, cream gels or pastes. They may optionally be packaged as an aerosol and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", the aerosol containers comprising a propellant, and also aerosol pumps using compressed air as propellant. These pumps are described in U.S. Pat. Nos. 4,077,441 and 4,850,517 (which form an integral part of the content of the description).

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

A person skilled in the art will select said active agent or agents as a function of the desired effect on the skin, hair, eyelashes, eyebrows or nails. It will be possible for the composition further to comprise at least one ingredient such as soft-focus effect fillers or agents which promote the natural colouring of the skin, for the purpose of complementing the biological effect of these active agents or providing an immediate visual anti-ageing effect.

Other Additional Ingredients

It will be possible for the composition further to comprise at least one additional ingredient intended for complementing the biological effect of these active agents or for providing an immediate visual effect; mention may be made especially of matifying agents, soft-focus effect fillers, fluorescent agents, agents for promoting the naturally pinkish coloration of the skin, and abrasive or exfoliating fillers.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be taken up by the biological effect of the active agents mentioned above. They may also, via a mechanical action (e.g.: abrasive fillers), amplify the effect of the biological active agents mentioned above.

Thus the composition according to the invention may further comprise at least one agent chosen from matifying agents, fillers with a soft-focus effect, agents for promoting the naturally pinkish coloration of the skin, abrasive fillers or exfoliants, and mixtures thereof.

Matifying Agents

The term "matifying agent" means agents intended to make the skin visibly more matt and less shiny.

The matifying effect of the agent and/or composition containing it may especially be evaluated using a gonioreflectometer, by measuring the ratio R between the specular reflection and the scattered reflection. A value of R of less than or equal to 2 generally reflects a matifying effect.

The matifying agent may especially be chosen from a rice starch or a corn starch (INCI name: Zea Mays (corn) Starch such as, in particular, the product sold under the trade name "Farmal CS 3650 Plus 036500" by National Starch), kaolinite, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matifying agents that may especially be mentioned include:

rice or corn starch, in particular an aluminium starch octenyl succinate sold under the name Dry Flo® by the company National Starch;

kaolinite;

silicas;

talc;

a pumpkin seed extract as sold under the name Curbilene® by the company Indena;

cellulose microbeads as described in patent application EP 1 562 562;

fibres, such as silk fibres, cotton fibres, wool fibres, flax fibres, cellulose fibres extracted especially from wood, from vegetables or from algae, polyamide (Nylon®) fibres, modified cellulose fibres, poly(p-phenylene terephthalamide) fibres, acrylic fibres, polyolefin fibres, glass fibres, silica fibres, aramid fibres, carbon fibres, Teflon® fibres, insoluble collagen fibres, polyester fibres, polyvinyl chloride or polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in patent application EP 1 151 742;

expanded acrylic copolymer microspheres such as those sold by the company EXPANCEL under the name Expancel 551®;

fillers with an optical effect as described in patent application FR 2 869 796, in particular:

polyamide (Nylon®) powders, for instance Nylon-12 particles of the Orgasol type from Arkema, with a mean size of 10 microns and a refractive index of 1.54, silica powders, for instance Silica beads SB150 from Miyoshi with a mean size of 5 microns and a refractive index of 1.45, polytetrafluoroethylene powders, for instance PTFE Ceridust 9205F from Clariant, with a mean size of 8 microns and a refractive index of 1.36, silicone resin powders, for instance the silicone resin Tospearl 145A from GE Silicone with a mean size of 4.5 microns and a refractive index of 1.410, acrylic copolymer powders, especially of polymethyl (meth)acrylate, for instance the PMMA particles Jurymer MBI from Nihon Junyoki, with a mean size of 8 microns and a refractive index of 1.49, or the Micropearl M100® and F 80 ED® particles from the company Matsumoto Yushi-Seiyaku, wax powders, for instance the paraffin wax particles Microease 114S from Micropowders, with a mean size of 7 microns and a refractive index of 1.54, polyethylene powders, especially comprising at least one ethylene/acrylic acid copolymer, and in particular constituted of ethylene/acrylic acid copolymers, for instance the particles Flobeads EA 209 from Sumitomo (with a mean size of 10 microns and a refractive index of 1.48), elastomeric crosslinked organopolysiloxane powders coated with silicone resin, especially with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and talc/titanium dioxide/alumina/silica composite powders such as those sold under the name Coverleaf® AR-80 by the company Catalyst & Chemicals, mixtures thereof, compounds that absorb and/or adsorb sebum as described in patent application FR 2 869 796. Mention may be made especially of:

silica powders, for instance the porous silica microspheres sold under the name Silica Beads SB-700 sold by the company Miyoshi, the products Sunsphere®H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass;

amorphous mixed silicate powders, especially of aluminium and magnesium, for instance the product sold under the name Neusilin UFL2 by the company Sumitomo;

polyamide (Nylon®) powders, for instance Orgasol® 4000 sold by the company Arkema, and acrylic polymer powders, especially of polymethyl methacrylate, for instance Covabead® LH85 sold by the company Wackherr; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;

silicate particles, such as alumina silicate;

mixed silicate particles, such as:

magnesium aluminium silicate particles, such as saponite or hydrated magnesium aluminium silicate with a sodium sulphate sold under the trade name Sumecton® by the company Kunimine;

the magnesium silicate, hydroxyethyl cellulose, black cumin oil, marrow oil and phospholipids complex or Matipure® from Lucas Meyer, and mixtures thereof.

Preferred matifying agents that may be used according to the invention include a pumpkin seed extract, a rice or corn starch, kaolinite, silicas, talc, polyamide powders, polyethylene powders, acrylic copolymer powders, expanded acrylic copolymer microspheres, silicone resin microbeads and mixed silicate particles, and mixtures thereof.

Fillers with a Soft-focus Effect

These fillers may be any material capable of modifying and hiding wrinkles by virtue of their intrinsic physical properties. These fillers may especially modify wrinkles via a tensioning effect, a covering effect or a soft-focus effect.

Examples of fillers that may be given include the following compounds:

porous silica microparticles, for instance Silica Beads® SB150 and SB700 from Miyoshi with a mean size of 5 µm; the Sunspheres® H series from Asahi Glass, for instance Sunspheres H33, H51 with respective sizes of 3.5 and 5 µm;

hollow hemispherical silicone resin particles such as NLK 500®, NLK 506® and NLK 510® from Takemoto Oil and Fat, especially described in EP-A-1 579 849;

silicone resin powders, for instance the silicone resin Tospearl® 145A from GE Silicone, with a mean size of 4.5 µm;

acrylic copolymer powders, especially of polymethyl (meth)acrylate, for instance the PMMA particles Jurimer MBI® from Nihon Junyoki, with a mean size of 8 μm, the hollow PMMA spheres sold under the name Covabead® LH85 by the company Wackherr, and vinylidene/acrylonitrile/methylene methacrylate expanded microspheres sold under the name Expance®;

wax powders, for instance the paraffin wax particles MicroEase® 114S from Micropowders, with a mean size of 7 μm;

polyethylene powders, especially comprising at least one ethylene/acrylic acid copolymer, for instance Flobeads® EA 209 E from Sumitomo, with a mean size of 10 μm;

crosslinked elastomeric organopolysiloxane powders coated with silicone resin and especially with silsesquioxane resin, sold under the names KSP-100®, KSP-101®, KSP-102®, KSP-103®, KSP-104® and KSP-105® by the company Shin-Etsu;

talc/titanium dioxide/alumina/silica composite powders, for instance Coverleaf AR 80® from the company Catalyst & Chemical;

talc, mica, kaolin, lauryl glycine, starch powders crosslinked with octeanyl succinate anhydride, boron nitride, polytetrafluoroethylene powders, precipitated calcium carbonate, magnesium carbonate, magnesium hydrogen carbonate, barium sulphate, hydroxyapatite, calcium silicate, cerium dioxide and glass or ceramic microcapsules;

hydrophilic or hydrophobic, synthetic or natural, mineral or organic fibres such as silk fibres, cotton fibres, wool fibres, flax fibres, cellulose fibres extracted especially from wood, vegetables or algae, polyamide (Nylon®) fibres, modified cellulose fibres, poly(p-phenylene terephthalamide) fibres, acrylic fibres, polyolefin fibres, glass fibres, silica fibres, aramid fibres, carbon fibres, polytetrafluoroethylene (Teflon®) fibres, insoluble collagen fibres, polyester fibres, polyvinyl chloride fibres, polyvinylidene chloride fibres, polyvinyl alcohol fibres, polyacrylonitrile fibres, chitosan fibres, polyurethane fibres, polyethylene phthalate fibres, fibres formed from a mixture of polymers, resorbable synthetic fibres, and mixtures thereof described in patent application EP 1 151 742;

spherical elastomeric crosslinked silicones, for instance Trefil E-505C or E-506C from Dow Corning;

abrasive fillers, which, via a mechanical effect, smooth out the skin microrelief, such as abrasive silica, for instance Abrasif SP® from Semanez or nut or shell powders (for example of apricot or walnut, from Cosmetochem).

The fillers with an effect on the signs of ageing are especially chosen from porous silica microparticles, hollow hemispherical silicone particles, silicone resin powders, acrylic copolymer powders, polyethylene powders, crosslinked elastomeric organopolysiloxane powders coated with silicone resin, talc/titanium dioxide/alumina/silica composite powders, precipitated calcium carbonate, magnesium carbonate, magnesium hydrogen carbonate, barium sulphate, hydroxyapatite, calcium silicate, cerium dioxide, glass or ceramic microcapsules, and silk fibres or cotton fibres, and mixtures thereof.

The filler may be a soft-focus filler.

The term "soft-focus" filler means a filler which in addition gives the complexion transparency and a hazy effect. Preferably, the soft-focus fillers have a mean particle size of less than or equal to 15 microns. These particles may be in any form and in particular may be spherical or non-spherical. These fillers are more preferably non-spherical.

The soft-focus fillers may be chosen from silica and silicate powders, especially alumina powder, powders of polymethyl methacrylate (PMMA) type, talc, silica/$TiO_2$ or silica/zinc oxide composites, polyethylene powders, starch powders, polyamide powders, styrene/acrylic copolymer powders and silicone elastomers, and mixtures thereof.

Mention may be made in particular of talc with a number-average size of less than or equal to 3 microns, for example talc with a number-average size of 1.8 microns and especially the product sold under the trade name Talc P3® by the company Nippon Talc, Nylon®-12 powder, especially the product sold under the name Orgasol 2002 Extra D Nat Cos® by the company Atochem, silica particles 1% to 2% surface-treated with a mineral wax (INCI name: hydrated silica (and) paraffin) such as the products sold by the company Degussa, amorphous silica microspheres, such as the products sold under the name Sunsphere, for example of reference H-53® by the company Asahi Glass, and silica microbeads such as those sold under the name SB-700® or SB-150® by the company Miyoshi, this list not being limiting.

The concentration of these fillers with an effect on the signs of ageing in the compositions according to the invention may be between 0.1% and 40%, or even between 0.1% and 20% by weight, relative to the total weight of the composition.

Agents for Promoting the Naturally Pinkish Coloration of the Skin

Mention may be made especially of:

a self-tanning agent, i.e. an agent which, when applied to the skin, especially to the face, can produce a tan effect that is more or less similar in appearance to that which may result from prolonged exposure to the sun (natural tan) or under a UV lamp;

an additional colouring agent, i.e. any compound that has a particular affinity for the skin, which allows it to give the skin a lasting, non-covering coloration (i.e. that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment;

and mixtures thereof.

Examples of self-tanning agents that may especially be mentioned include:

dihydroxyacetone (DHA), erythrulose, and the combination of a catalytic system formed from:

manganese and/or zinc oxides and salts, and alkali metal and/or alkaline-earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxy-acetone (DHA) and 4,4-dihydroxy-pyrazolin-5-one derivatives as described in patent application EP 903 342. DHA will preferably be used.

The DHA may be used in free and/or encapsulated form, for example in lipid vesicles such as liposomes, especially described in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluoran type such as those described in patent application FR 2 840 806. Mention may be made, for example, of the following dyes:

- tetrabromofluorescein or eosin known under the CTFA name: CI-45380 or Red 21;
- phloxin B known under the CTFA name: CI-45410 or Red 27;
- diiodofluorescein known under the CTFA name: CI-45425 or Orange 10;
- dibromofluorescein known under the CTFA name: CI-45370 or Orange 5;
- the sodium salt of tetrabromofluorescein known under the CTFA name: CI-45380 (Na salt) or Red 22;
- the sodium salt of phloxin B known under the CTFA name: CI-45410 (Na salt) or Red 28;
- the sodium salt of diiodofluorescein known under the CTFA name: CI-45425 (Na salt) or Orange 11;
- erythrosine known under the CTFA name: CI-45430 or Acid Red 51;
- phloxin known under the CTFA name: CI-45405 or Acid Red 98.

These dyes may also be chosen from anthraquinones, caramel, carmine, carbon black, azulene blues, methoxalene, trioxalene, guajazulene, chamuzulene, Bengal rose, cosin 10B, cyanosin and daphinin.

These dyes may also be chosen from indole derivatives, for instance the monohydroxyindoles as described in patent FR 2 651 126 (i.e.: 4-, 5-, 6- or 7-hydroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants

As exfoliants that may be used in rinse-out compositions according to the invention, examples that may be mentioned include exfoliating or scrubbing particles of mineral, plant or organic origin. Thus, polyethylene beads or powder, Nylon powder, polyvinyl chloride powder, pumice, ground apricot kernel or walnut shell, sawdust, glass beads and alumina, and mixtures thereof, may be used, for example. Mention may also be made of Exfogreen® from Solabia (bamboo extract), extracts of strawberry achenes (Strawberry Achenes from Greentech), peach kernel powder, apricot kernel powder, and finally, in the field of plant powders with an abrasive effect, mention may be made of cranberry kernel powder.

As abrasive fillers or exfoliants that are preferred according to the invention, mention will be made of peach kernel powder, apricot kernel powder, cranberry kernel powder, strawberry achene extracts and bamboo extracts.

The following examples serve to illustrate the invention without however exhibiting a limiting character. In these examples the amounts of the composition ingredients are given as weight percentages relative to the total weight of the composition.

EXAMPLES 1 AND 2

Antisun formulations containing the following ingredients were prepared.

| Ingredients | Ex. 1 | Ex. 2 (*) |
|---|---|---|
| Phase A | | |
| DEMINERALIZED WATER | 36.25 | 36.25 |
| GLYCEROL | 5.0 | 5.0 |
| ZINGERONE | 2.0 | — |
| Phase B$_1$ | | |
| SORBITAN TRISTEARATE (SPAN 65 V - CRODA) | 0.9 | 0.9 |
| PEG-40 STEARATE (MYRJ S40-PA-(WL)- CRODA) | 2.0 | 2.0 |
| CETYL ALCOHOL | 4.0 | 4.0 |
| GLYCERYL STEARATE SE (TEGIN PELLETS - EVONIK GOLDSCHMIDT) | 3.0 | 3.0 |
| STEARIC ACID | 1.3 | 1.3 |
| PETROLATUM | 4.0 | 4.0 |
| MYRISTYL MYRISTATE | 2.0 | 2.0 |
| BUTYL METHOXY DIBENZOYLMETHANE (PARSOL 1789 - DSM) | 3.0 | 3.0 |
| OCTOCRYLENE (UVINUL N539 - BASF) | 7.0 | 7.0 |
| OCTYL SALICYLATE (NEO HELIOPAN OS - SYMRISE) | 5.0 | 5.0 |
| CYCLOHEXASILOXANE (SILSOFT 1217 - DOW CORNING) | 7.0 | 7.0 |
| Phase B$_2$ | | |
| TOCOPHEROL | 0.05 | 0.05 |
| Phase C | | |
| ACRYLAMIDE/SODIUM ACRYLOYLDIMETHYL-TAURATE COPOLYMER (and) ISOHEXADECANE (and) POLYSORBATE 80 (SIMULGEL - SEPPIC) | 1.3 | 1.3 |
| Phase D | | |
| SILICA MICROSPHERES (PARTICLE SIZE: 3 MICRONS) (MSS 500/3 - KOBO) | 2.0 | 2.0 |
| Phase E | | |
| VICHY WATER | 5 | 5 |
| Phase F | | |
| TRIETHANOLAMINE | 0.2 | 0.2 |
| DEMINERALIZED WATER | qs for 100 | qs for 100 |

(*) outside the invention

The aqueous phase A is prepared, which is heated at 80/85° C. (cloudy solution)—then the temperature is reduced to around 70° C. (68° C.)

The fatty phase B1 is prepared, then it is heated at 68/72° C. (72° C.—clear). The phase B2 is added at 68° C.

An emulsion is formed by incorporating the phase B into the phase A over 10 min at 2500 rpm—(microscope: fine and dense emulsion with some large globules).

At a temperature of 50° C., the phase C is incorporated into the mixture AB up to 3300 rpm (blockage of the emulsifier). It is then moved into a mixer for around 10 min to refine the large globules. It is cooled using a butterfly shaft to around 40° C. The phases D, E and F are subsequently added over 10 min.

For each of the compositions 1 and 2, the sun protection factor (SPF) associated therewith was then determined. This was determined by using the in vitro method described by V. Wandel et al. in SÖFW Journal 127 (2001); this method consists in determining the monochromatic protection factors over a wavelength range from 290 to 400 nm and in calculating therefrom the sun protection factor according to a given mathematical equation. The measurement was performed with a 1 nm interval on a UV-1000S machine from the company Labsphere, 0.6 mg/cm² of product being spread onto a frosted PMMA plate. The results (mean value corresponding to 5 plates per product, 10 points per plate) are collated in Table (I) below:

TABLE (I)

| Composition | 1 (invention) with gingerone | 2 (outside the invention) without gingerone |
| --- | --- | --- |
| Average SPF | 28.86 | 24.06 |
| Coefficient of variation | 12.4 | 9.7 |

The two averages are significantly different at 95% and 99% confidence according to the Student's t-test.

The invention claimed is:

1. A fluid ultraviolet radiation protection composition for protecting the skin and/or hair against ultraviolet radiation, which comprises, in a cosmetically acceptable aqueous support:
   (a) at least one photoprotective system capable of screening out UV radiation constituted by one or more hydrophilic, lipophilic or insoluble organic screening agents and/or one or more metal oxide pigments which may or may not be coated; and
   (b) at least one 2-alkoxy-4-alkyl ketone phenol compound.

2. The composition according to claim 1, where the 2-alkoxy-4-alkyl ketone phenol compound is selected from the group consisting of compounds represented by the formula (I) below:

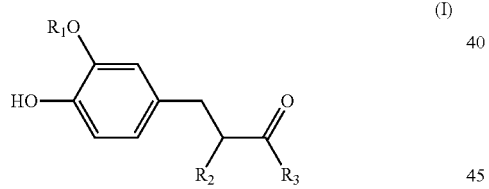

(I)

in which
   $R_1$ represents a linear $C_1$-$C_4$ alkyl radical;
   $R_2$ represents a hydrogen atom or a linear $C_1$-$C_4$ alkyl radical; and
   $R_3$ represents a linear $C_1$-$C_{12}$ alkyl radical, optionally substituted by a hydroxyl group; or a linear $C_2$-$C_{12}$ alkenyl radical, optionally substituted by a hydroxyl group.

3. The composition according to claim 2, where the 2-alkoxy-4-alkyl ketone phenol compound is selected from the group consisting of compounds represented by formula (I) for which:
   $R_2$ is chosen from H and $CH_3$; and/or
   $R_3$ represents (i) a $C_1$-$C_{10}$ alkyl radical; (ii) a $C_2$-$C_{10}$ alkenyl radical; or (iii) a hydroxyalkyl radical of structure —$CH_2$—CH(OH)—$R_5$ with $R_5$ representing a linear $C_1$-$C_{10}$ alkyl radical.

4. The composition according claim 1, where the 2-alkoxy-4-alkyl ketone phenol compound is selected from the group consisting of the following compounds:

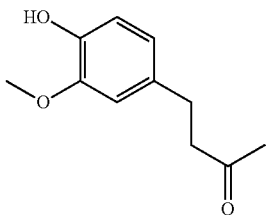

(a)

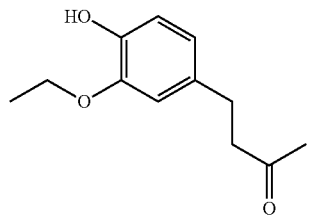

(b)

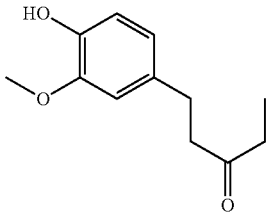

(c)

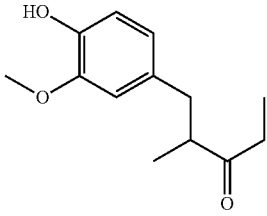

(d)

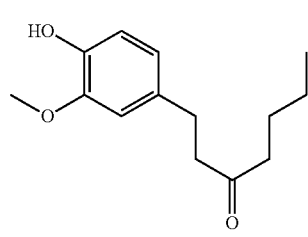

(e)

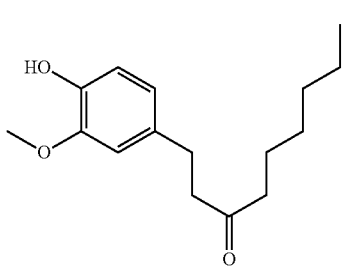

(f)

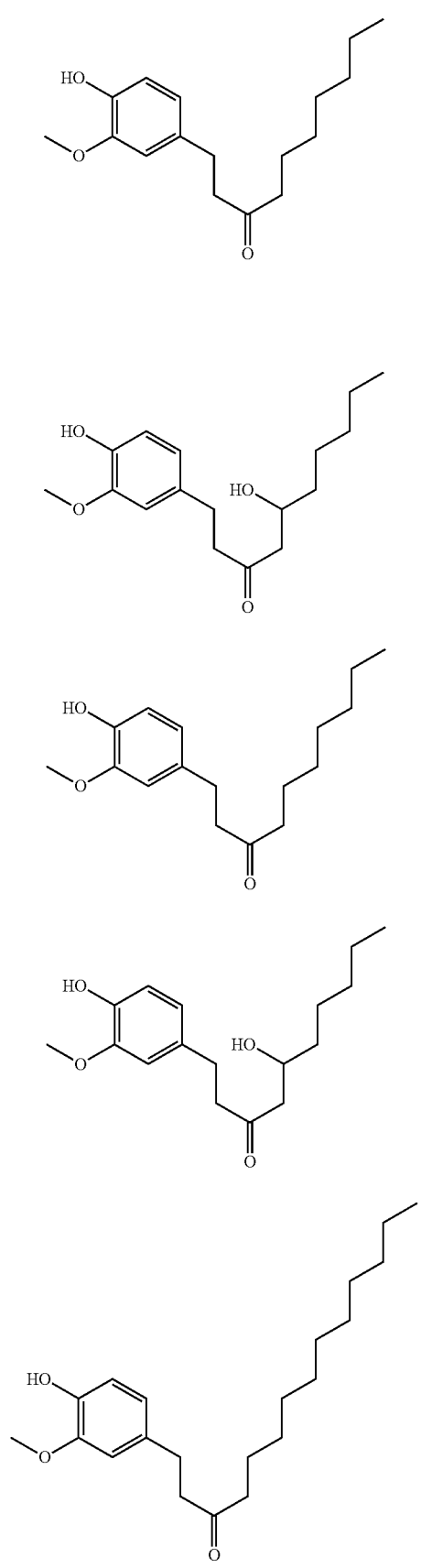
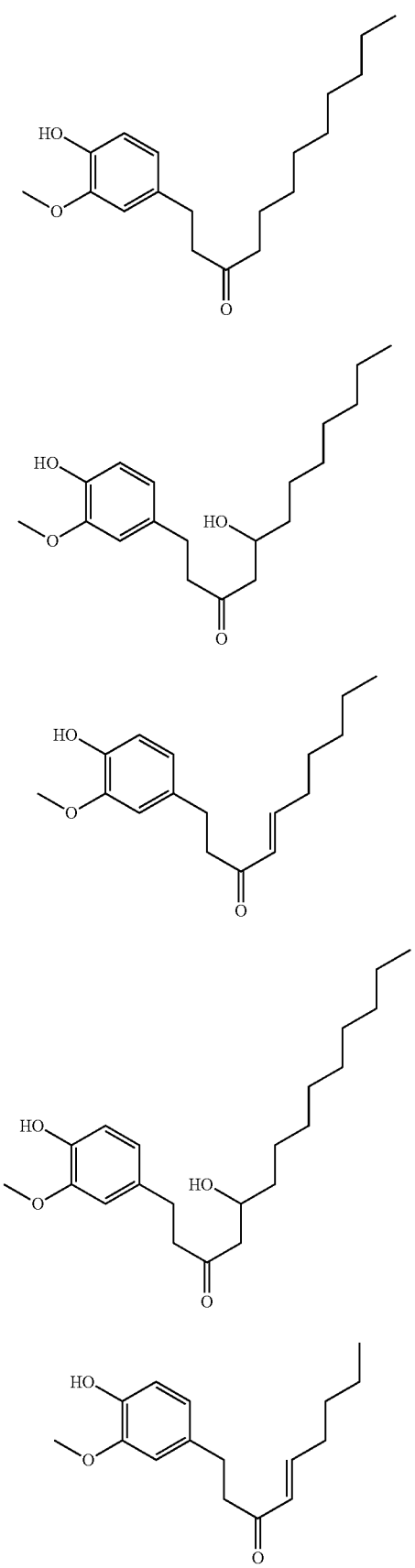

-continued

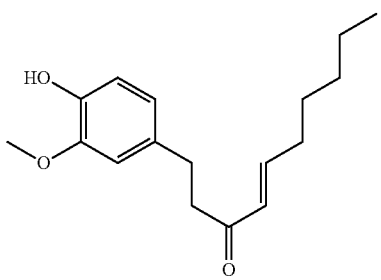

(q)

5. The composition according to claim 1, where the 2-alkoxy-4-alkyl ketone phenol compound is the 4-(3-methoxy-4-hydroxyphenyl) butan-2-one compound of formula (a)

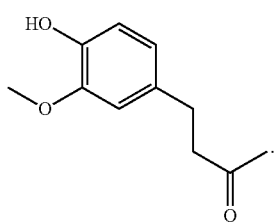

(a)

6. The composition according to claim 1, where the 2-alkoxy-4-alkyl ketone phenol compound(s) is (are) present in concentrations ranging from 0.01 to 10% by weight relative to the total weight of the composition.

7. The composition according to claim 1, where the organic UV screening agents are selected from the group consisting of cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzoazolyl derivatives; p-aminobenzoic acid (PABA) derivatives; methylene bis-(hydroxyphenylbenzotriazole) derivatives; benzoxazole derivatives; screening polymers and screening silicones; dimers derived from a-alkylstyrene; 4,4-diarylbutadienes; merocyanine derivatives; and mixtures thereof.

8. The composition according to claim 7, where organic UV screening agents are selected from the group consisting of:
Ethylhexyl Methoxycinnamate,
Homosalate,
Ethylhexyl Salicylate,
Octocrylene,
Butyl Methoxydibenzoylmethane,
Terephthalylidene Dicamphor Sulfonic Acid, Disodium Phenyl Dibenzimidazole Tetrasulfonate, Phenylbenzimidazole Sulfonic Acid,
Benzophenone-3,
n-Hexyl 2-(4-diethylamino-2-hydroxybenzoyl)-benzoate,
4-Methylbenzylidene Camphor,
Ethylhexyl triazone,
Bis-Ethylhexyloxyphenol Methoxyphenyl Triazine, Diethylhexyl Butamido Triazone,
2,4-bis(n-butyl 4'-aminobenzalmalonate)-6-[(3-{1,3,3,3-tetramethyl-1-[(trimethylsilyl)oxy]disiloxanyl}propyl) amino]-s-triazine,
2,4,6-Tris(biphenyl-4-yl)-1,3,5-triazine,
2,4,6-Tris(dineopentyl 4'-aminobenzalmalonate)-triazine,
2,4,6-Tris(diisobutyl 4'-aminobenzalmalonate)-s triazine,
2,4-Bis(dineopentyl 4'-aminobenzalmalonate)-6-(butyl 4'-aminobenzoate)-s-triazine,
Methylene Bis-Benzotriazolyl Tetramethylbutyl-phenol,
Drometrizole Trisiloxane,
Polysilicone-15,
Di-neopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl) imino]-6-(2-ethylhexyl) imino-1,3,5-triazine, and mixtures thereof.

9. The composition according to claim 1, where the metal oxide particles have a mean elementary particle size of less than or equal to 500 nm.

10. The composition according to claim 9, where the metal oxide particles are selected from the group consisting of titanium oxides, zinc oxides, iron oxides, zirconium oxides, cerium oxides and mixtures thereof.

11. A method of increasing the sun protection factor (SPF) of a fluid ultraviolet radiation protection composition which comprises including a 2-alkoxy-4-alkyl ketone phenol compound according to claim 1, in a composition comprising, in a cosmetically acceptable aqueous support, at least one photoprotective system capable of screening out UV radiation.

12. The composition according to claim 3, where $R_5$ represents a linear $C_4$-$C_{10}$ alkyl radical.

13. Composition according claim 6, where the 2-alkoxy-4-alkyl ketone phenol compound is chosen from the following compounds:

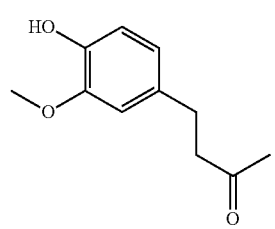

(a)

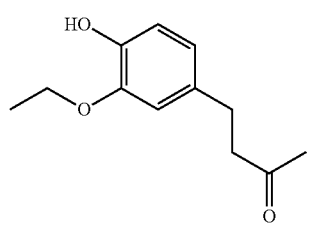

(b)

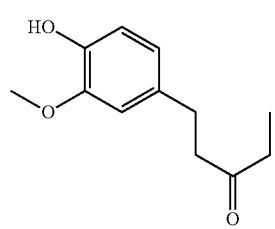

(c)

-continued
(d)
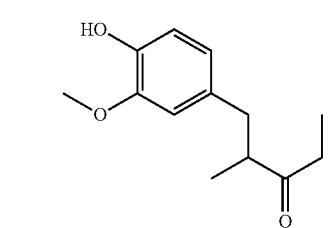
(e)
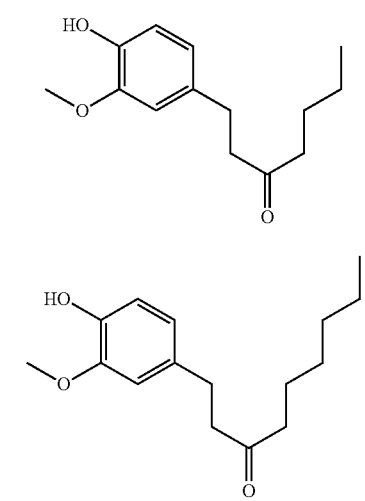
(f)
(g)
(h)
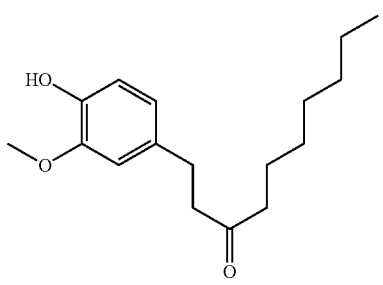
(i)
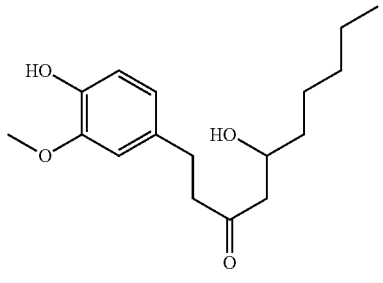
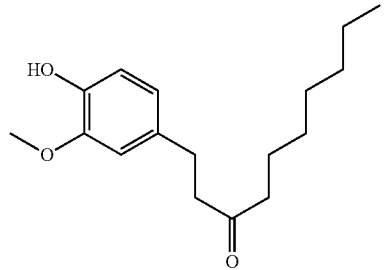
-continued
(j)
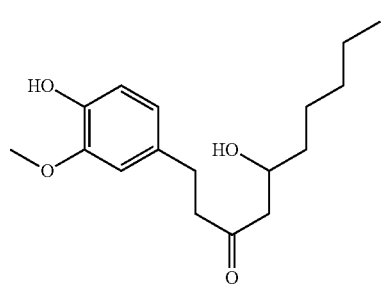
(k)
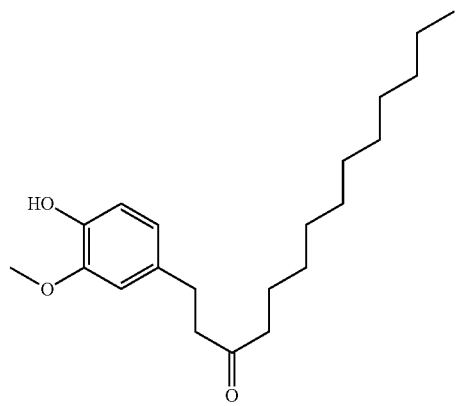
(l)
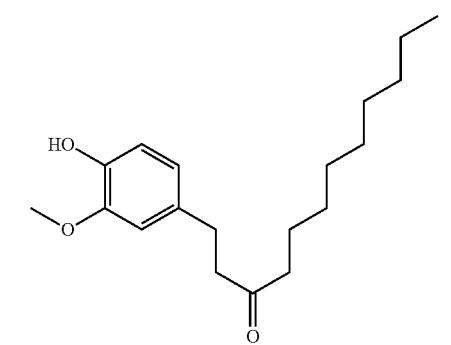
(m)
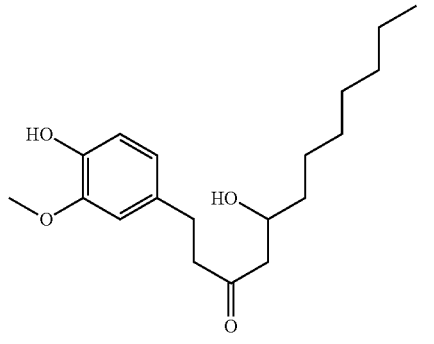
(n)
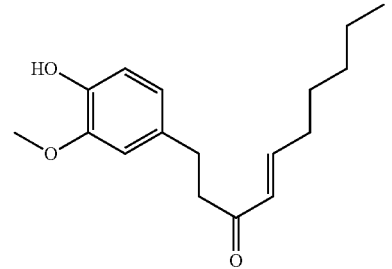

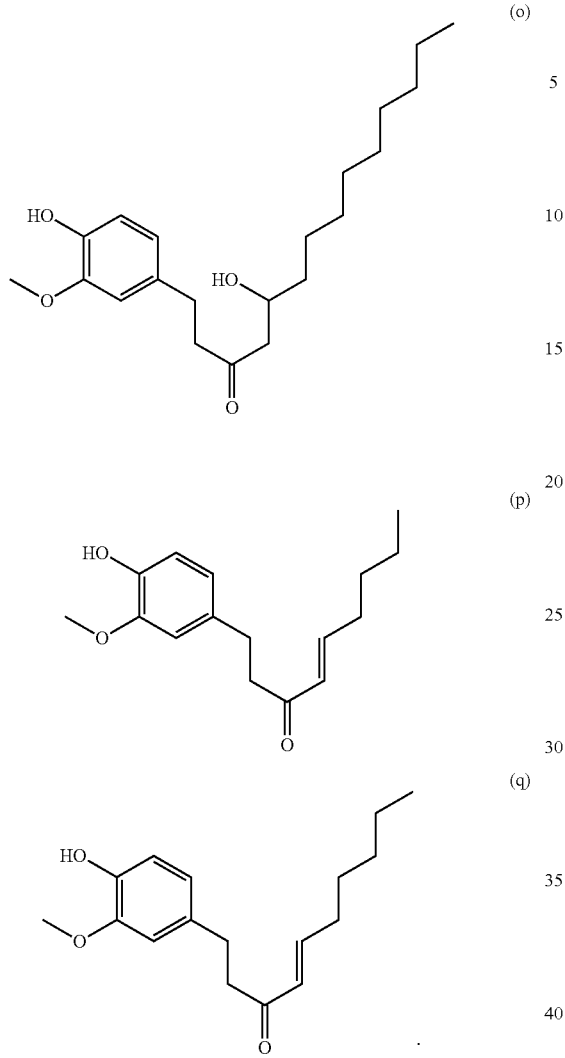
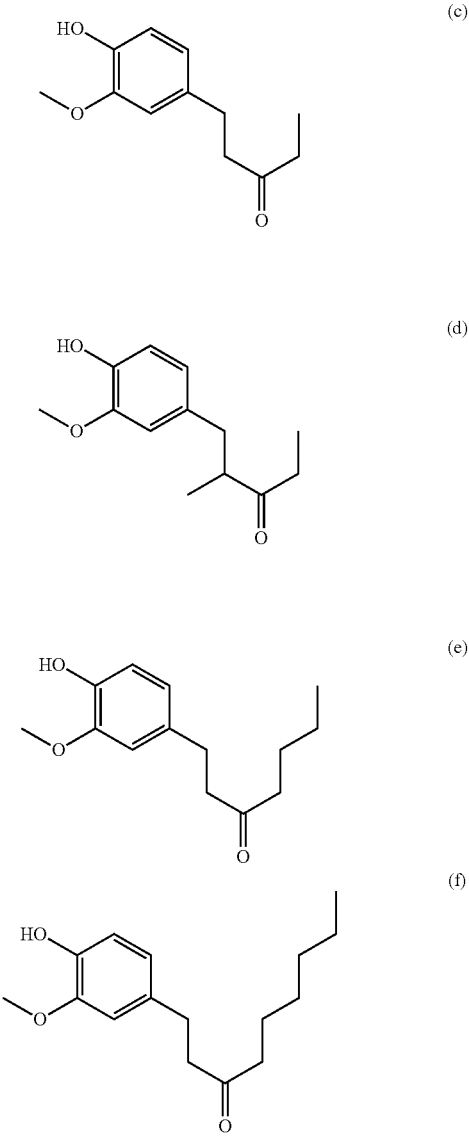
14. Composition according to claim 7, where the 2-alkoxy-4-alkyl ketone phenol compound is chosen from the following compounds:
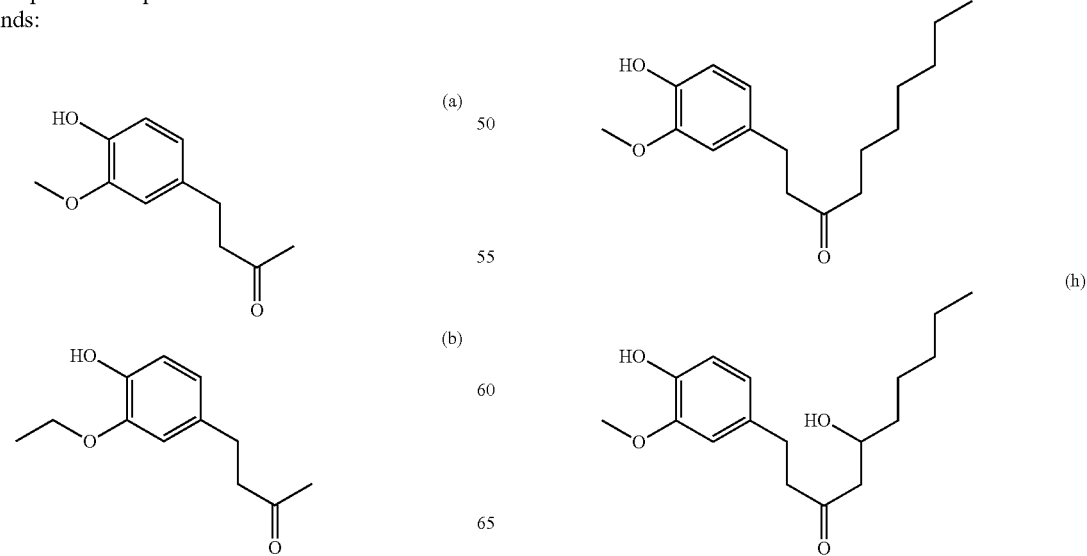

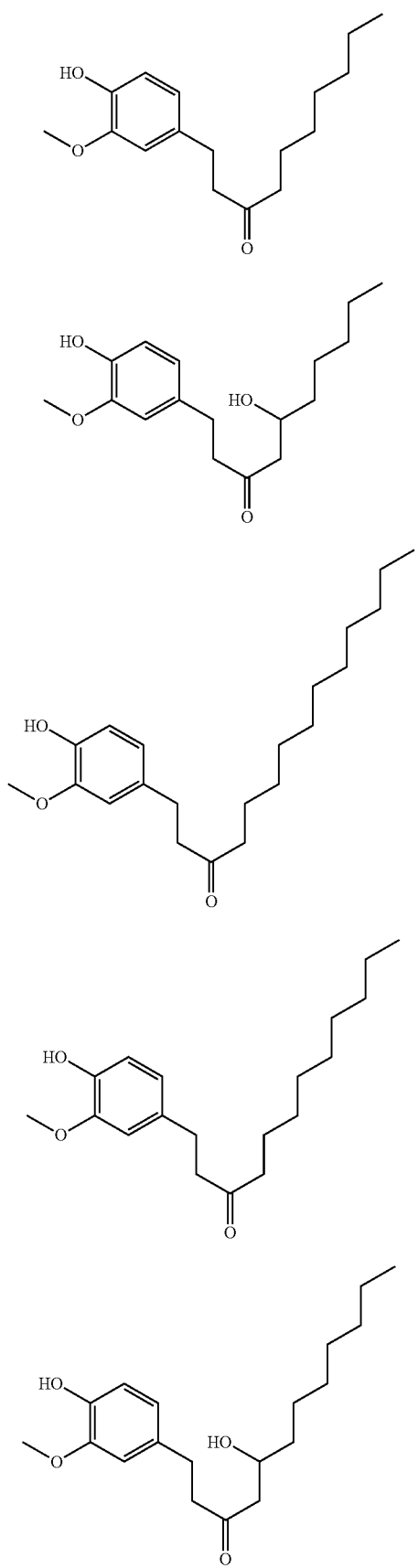
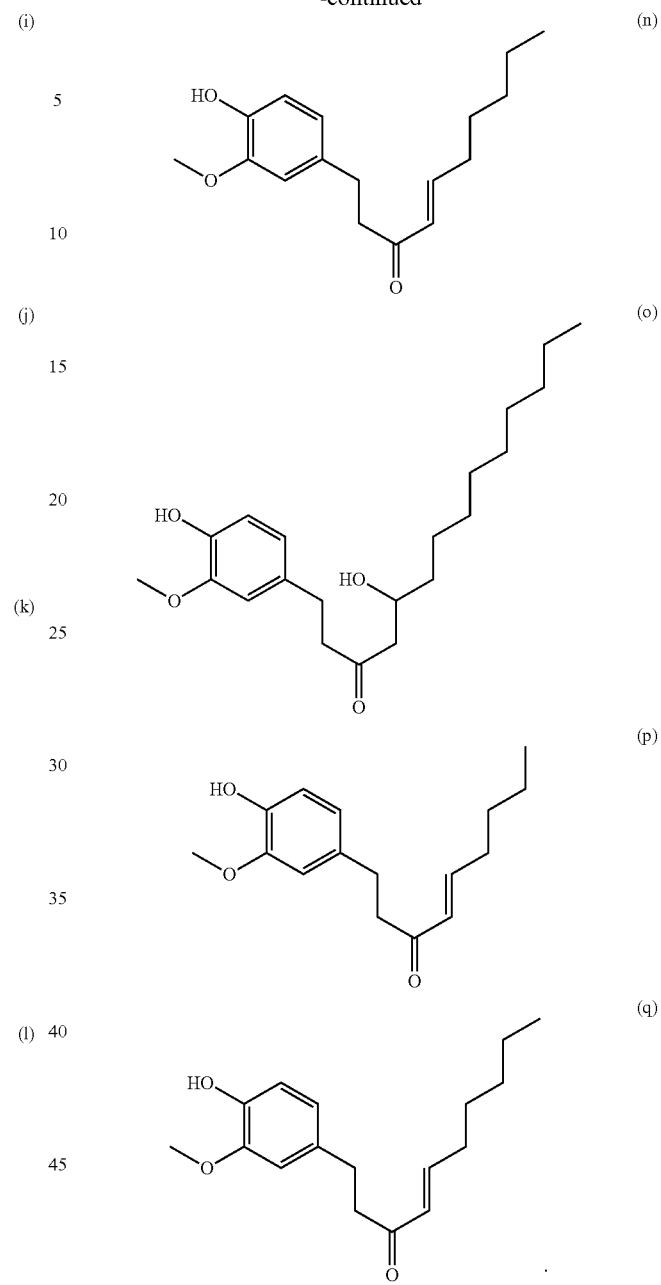

15. Composition according to claim 1, where the 2-alkoxy-4-alkyl ketone phenol compound (s) is (are) present in concentrations ranging from 0.5 to 5% relative to the total weight of the composition.

16. The composition according to claim 1, where the 2-alkoxy-4-alkyl ketone phenol compound (s) is (are) present in concentrations ranging from 1 to 3% relative to the total weight of the composition.

17. The composition according to claim 1, where the metal oxide particles have a mean elementary particle size of between 5 nm and 500 nm.

18. The composition according to claim 1, where the metal oxide particles have a mean elementary particle size of between 10 nm and 100 nm.

19. The composition according to claim 1, where the metal oxide particles have a mean elementary particle size of 15 nm and 50 nm.

20. The composition according to claim 6, where the 2-alkoxy-4-alkyl ketone phenol compound is the 4-(3-methoxy-4-hydroxyphenyl) butan-2-one compound of formula (a)
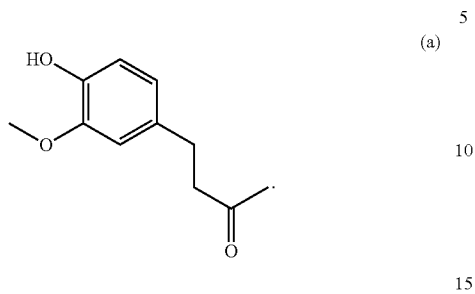
(a)
21. The composition according to claim 1, where the 2-alkoxy-4-alkyl ketone phenol compound is the ethyl gingerone of structure (b)
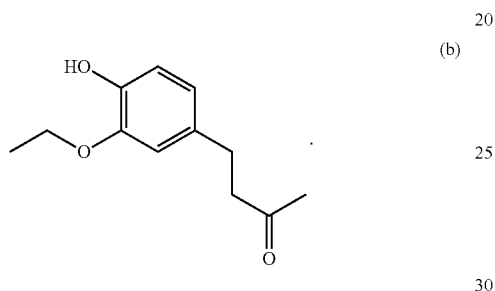
(b)
* * * * *